(12) United States Patent
Yagyu et al.

(10) Patent No.: US 10,910,210 B2
(45) Date of Patent: Feb. 2, 2021

(54) ULTRAVIOLET STERILIZER

(71) Applicant: Ushio Denki Kabushiki Kaisha, Tokyo (JP)

(72) Inventors: Hideaki Yagyu, Tokyo (JP); Ryosuke Ikeno, Tokyo (JP); Masahiro Sasaki, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/471,043

(22) PCT Filed: Jan. 10, 2018

(86) PCT No.: PCT/JP2018/000243
§ 371 (c)(1),
(2) Date: Jun. 19, 2019

(87) PCT Pub. No.: WO2018/131582
PCT Pub. Date: Jul. 19, 2018

(65) Prior Publication Data
US 2020/0234941 A1     Jul. 23, 2020

(30) Foreign Application Priority Data

Jan. 10, 2017  (JP) .................. 2017-001592
Jan. 20, 2017  (JP) .................. 2017-008220

(51) Int. Cl.
*H01J 61/02*     (2006.01)
*A61L 2/00*      (2006.01)
(Continued)

(52) U.S. Cl.
CPC .......... *H01J 61/025* (2013.01); *A61L 2/0047* (2013.01); *A61L 2/26* (2013.01); *G02B 5/208* (2013.01); *H01J 61/52* (2013.01); *A61L 2202/11* (2013.01)

(58) Field of Classification Search
USPC ................................... 250/455.11
See application file for complete search history.

(56) References Cited

U.S. PATENT DOCUMENTS 3,136,890 A  *  6/1964  Wain ............... G01N 21/64
                                                250/504 H
4,049,987 A     9/1977  Helms
(Continued)

FOREIGN PATENT DOCUMENTS

JP       S52151269 A      12/1977
JP       H09-092225 A     4/1997
(Continued)

OTHER PUBLICATIONS

Buananno; et.al., "207-nm UV Light—A Promising Tool for Safe Low-Cost Reduction of Surgical Site Infections. I: In Vitro Studies" PLOS| one, Public Library of Science (PLOS), Oct. 2013,| vol. 8, Issue 10, pp. 1-7. (Year: 2013).*
(Continued)

*Primary Examiner* — Phillip A Johnston
(74) *Attorney, Agent, or Firm* — Studebaker & Brackett PC

(57) ABSTRACT

The present invention has as its object the provision of an ultraviolet sterilizer that can reduce ultraviolet light in a wavelength region of 230 to 300 nm, which is harmful to the human body, and can output effective light in a wavelength region of 200 to 230 nm with high emission intensity. The ultraviolet sterilizer of the present invention is an ultraviolet sterilizer comprising: an ultraviolet light source; a lamp storage chamber for storing the ultraviolet light source; and a light guiding part for guiding light from the ultraviolet light source, in which a band pass filter for reducing ultraviolet light in a wavelength region harmful to a human body is provided at least one of a position between the light guiding part and the lamp storage chamber and a position of (Continued)

a light outputting leading end of the light guiding part, and an inner surface of the light guiding part is formed from an ultraviolet absorbing member that absorbs the ultraviolet light in the wavelength region harmful to the human body.

11 Claims, 8 Drawing Sheets

(51) Int. Cl.
*A61L 2/26* (2006.01)
*G02B 5/20* (2006.01)
*H01J 61/52* (2006.01)

(56) References Cited

U.S. PATENT DOCUMENTS

| | | | | |
|---|---|---|---|---|
| 9,801,966 | B2* | 10/2017 | Garrett | G02B 27/141 |
| 2017/0081874 | A1* | 3/2017 | Daniels | E05B 1/0015 |
| 2017/0216466 | A1* | 8/2017 | Dujowich | A61L 2/0047 |
| 2017/0290932 | A1 | 10/2017 | Mori et al. | |
| 2018/0099061 | A1* | 4/2018 | Asano | A61L 2/10 |
| 2018/0243582 | A1 | 8/2018 | Kaneda et al. | |
| 2019/0038914 | A1 | 2/2019 | Igarashi et al. | |
| 2019/0091357 | A1* | 3/2019 | Matsumoto | A61L 2/24 |

FOREIGN PATENT DOCUMENTS

| | | |
|---|---|---|
| JP | 2006015051 A | 1/2006 |
| JP | 2017038671 A | 2/2017 |
| WO | 2016042879 A1 | 3/2016 |
| WO | 2017135190 A1 | 8/2017 |

OTHER PUBLICATIONS

International Search Report issued in PCT/JP2018/000243; dated Feb. 13, 2018.

An Office Action; "Notice of Reasons for Refusal," issued by the Japanese Patent Office dated May 21, 2019, which corresponds to Japanese Patent Application No. JP 2017-001592.

* cited by examiner (a) (b)

ULTRAVIOLET STERILIZER

TECHNICAL FIELD

The present invention relates to an ultraviolet sterilizer, and more specifically, to an ultraviolet sterilizer that can be preferably used, for example, for sterilizing the skin, body tissues, or the like.

BACKGROUND ART

Ultraviolet light has been preferably utilized, for example, for the sterilization of the skin or the like, deodorization, removal treatments of organic contaminants, and the like. Excimer lamps have been widely known as ultraviolet light sources (see Patent Literature 1, for example).

As a kind of excimer lamp, may be mentioned an excimer lamp having a light-emitting tube 51 made of synthetic quartz glass and having a double-tube structure including a cylindrical outer tube 52 and a cylindrical inner tube 53 disposed inside the outer tube 52 along its tube axis and having an outer diameter smaller than the inner diameter of the outer tube 52 as shown in FIG. 10. In this light-emitting tube 51, both ends of each of the outer tube 52 and the inner tube 53 are joined by sealing wall members 54A and 54B, and an annular internal space S1 is formed between the outer tube 52 and the inner tube 53. A discharge gas is charged in the internal space S1. In the light-emitting tube 51, a net-like outer electrode 55 is also provided on an outer peripheral surface of the outer tube 52, and a film-like inner electrode 56 is provided on an inner peripheral surface of the inner tube 53. The outer electrode 55 and the inner electrode 56 are each connected to a high-frequency power source 59.

In this excimer lamp 50, a high-frequency high-voltage is applied between the outer electrode 55 and the inner electrode 56 by the high-frequency power source 59. This generates excimer discharge in the internal space S1, and so excimer light is thereby emitted.

In sterilization by ultraviolet light (specifically, sterilization of the skin), ultraviolet light around a wavelength of 200 nm, specifically, ultraviolet light approximately within a wavelength range of 200 to 250 nm is used.

Since the excimer lamp can adjust wavelength characteristics (wavelength range) of emitted light by a kind of discharge gas, emitted light (ultraviolet light) having a center wavelength around a wavelength of 200 nm can be obtained by using an appropriate gas as a discharge gas. Specifically, as examples of a discharge gas for obtaining emitted light having a center wavelength around a wavelength of 200 nm (hereinafter, referred to also as a "specified discharge gas"), may be mentioned an argon fluoride (ArF) gas (the center wavelength of the resultant emitted light is 193 nm), a krypton bromide (KrBr) gas (the center wavelength of the resultant emitted light is 207 nm), a krypton chloride (KrCl) gas (the center wavelength of the resultant emitted light is 222 nm), a krypton fluoride (KrF) gas (the center wavelength of the resultant emitted light is 248 nm), a xenon iodide (XeI) gas (the center wavelength of the resultant emitted light is 253 nm) and a chlorine ($Cl_2$) gas (the center wavelength of the resultant emitted light is 259 nm).

CITATION LIST

Patent Literature

Patent Literature 1: Japanese Patent Application Laid-Open No. Hei. 9-92225

SUMMARY OF INVENTION

Technical Problem

Emitted light of an excimer lamp can be practically regarded as monochromatic light. While its spectrum (emitted spectrum) is a line spectrum, the spectrum has some spectral line width. Thus, the emitted light of the excimer lamp includes light at a center wavelength as well as light having a longer wavelength than the center wavelength and light having a shorter wavelength than the center wavelength. In the excimer lamp that emits ultraviolet light having a center wavelength of 222 nm, in particular, a small amount of light in a wavelength region of 230 to 300 nm, which is harmful to the human body, is also emitted.

Since the light in a wavelength region of 230 to 300 nm has harmful effects on the human body, such ultraviolet light in a wavelength region of 230 to 300 nm (hereinafter, referred to also as "harmful light"), which is harmful to the human body, needs to be blocked when the excimer lamp is used for the sterilization of the skin or medical treatment, for example.

A band pass filter (BPF) is typically used to block such harmful light.

Because of the characteristics of band pass filters, however, it is difficult to block harmful light in light having a large incidence angle.

FIG. 11 is a graph showing incidence angle dependence of light transmittance in a band pass filter designed to transmit light in a wavelength region around 222 nm.

When light has an incidence angle of 0°, i.e., when light is incident perpendicular to the plane of incidence (indicated by a solid line in FIG. 11), light in a wavelength region around 220 nm is transmitted and harmful light (ultraviolet light in a wavelength region of 230 to 300 nm) is blocked.

When light has an incidence angle of 40° (indicated by a dot-and-dash line in FIG. 11), on the other hand, light approximately in a wavelength region of not shorter than 210 nm and shorter than 280 nm is blocked and light in a wavelength region not shorter than 280 nm is transmitted. That is, the harmful light is transmitted without transmitting needed ultraviolet light in a wavelength region of 200 to 230 nm (hereinafter, referred to also as "effective light").

Furthermore, when light has an incidence angle of 60° (indicated by a broken line in FIG. 11), light approximately in a wavelength region of not shorter than 200 nm and shorter than 260 nm is blocked and light in a wavelength region not shorter than 260 nm is transmitted.

As described above, light transmittance of the band pass filter has angle dependence. As the incidence angle becomes larger, the wavelength region of the transmitted light moves (shifts) toward a shorter wavelength side. As a result, the band pass filter can transmit harmful light without transmitting the needed effective light.

The present invention has been made in view of the foregoing circumstances and has as its object the provision of an ultraviolet sterilizer that can reduce ultraviolet light in a wavelength region of 230 to 300 nm, which is harmful to the human body, and can output effective light in a wavelength region of 200 to 230 nm with high emission intensity.

Solution to Problem

An ultraviolet sterilizer of the present invention includes:
an ultraviolet light source;
a lamp storage chamber for storing the ultraviolet light source; and a light guiding part for guiding light from the ultraviolet light source, in which a band pass filter for reducing ultraviolet light in a wavelength region harmful to a human body is provided at least one of a position between the light guiding part and the lamp storage chamber and a position of a light outputting leading end of the light guiding part, and an inner surface of the light guiding part is formed from an ultraviolet absorbing member that absorbs the ultraviolet light in the wavelength region harmful to the human body.

In the ultraviolet sterilizer of the present invention, the band pass filter may preferably be a band pass filter that makes a light intensity ratio represented by the following Formula (1) not higher than 10%, light intensity ratio [%]={(intensity in an ultraviolet range having a wavelength region of 230 to 300 nm harmful to the human body)/(intensity in an effective light range having a wavelength region of 200 to 230 nm)}×100.   Formula (1):

In the ultraviolet sterilizer of the present invention, effective light in a wavelength region of 200 to 230 nm that has passed through the band pass filter may preferably be reflected by the ultraviolet absorbing member.

In the ultraviolet sterilizer of the present invention, the ultraviolet absorbing member may preferably be composed of glass.

In the ultraviolet sterilizer of the present invention, the ultraviolet light source may preferably be an excimer lamp having a center wavelength within a wavelength range of 190 to 260 nm.

The ultraviolet sterilizer of the present invention may be configured such that the light guiding part has a cylindrical body, the band pass filter or an irradiation window having an ultraviolet transmitting property is provided at a leading end of the cylindrical body, and an oxygen-containing layer is formed in the cylindrical body, and ultraviolet light having a wavelength at which the ultraviolet light generates ozone when absorbed by oxygen is absorbed in the oxygen-containing layer.

The ultraviolet sterilizer of the present invention may be configured such that a base end and the leading end of the cylindrical body are closed by the band pass filter and the irradiation window, and the oxygen-containing layer is airtightly formed between the band pass filter and the irradiation window.

In the ultraviolet sterilizer of the present invention, the band pass filter may preferably be provided at the position between the light guiding part and the lamp storage chamber, and the irradiation window may preferably be provided at the position of the light outputting leading end of the light guiding part.

In the ultraviolet sterilizer of the present invention, the lamp storage chamber may preferably have a cylindrical body, and at least one of an air exhaust fan and an air supply fan may preferably be provided at least one of one end and the other end of the cylindrical body in a cylinder axis direction thereof.

In the ultraviolet sterilizer of the present invention, an ozone filter may preferably be provided in an air flow passage including at least one of the air exhaust fan and the air supply fan provided in the cylindrical body.

Advantageous Effects of Invention

According to the ultraviolet sterilizer of the present invention, the band pass filter for reducing ultraviolet light in a wavelength region harmful to the human body is provided at least one of the position between the light guiding part and the lamp storage chamber and the position of the light outputting leading end of the light guiding part, and the inner surface of the light guiding part is formed from the ultraviolet absorbing member that absorbs the ultraviolet light in the wavelength region harmful to the human body. Thus, part of harmful light included in light from the ultraviolet light source is selectively blocked by the band pass filter, and the remaining part of the harmful light is absorbed by, or passes through, the ultraviolet absorbing member. As a result, in light outputted from the ultraviolet sterilizer of the present invention, emission intensity of harmful light can be reduced without significantly reducing emission intensity of ultraviolet light including effective light.

DESCRIPTION OF EMBODIMENTS

Embodiments of the present invention will be described below in detail.

Figure 1:
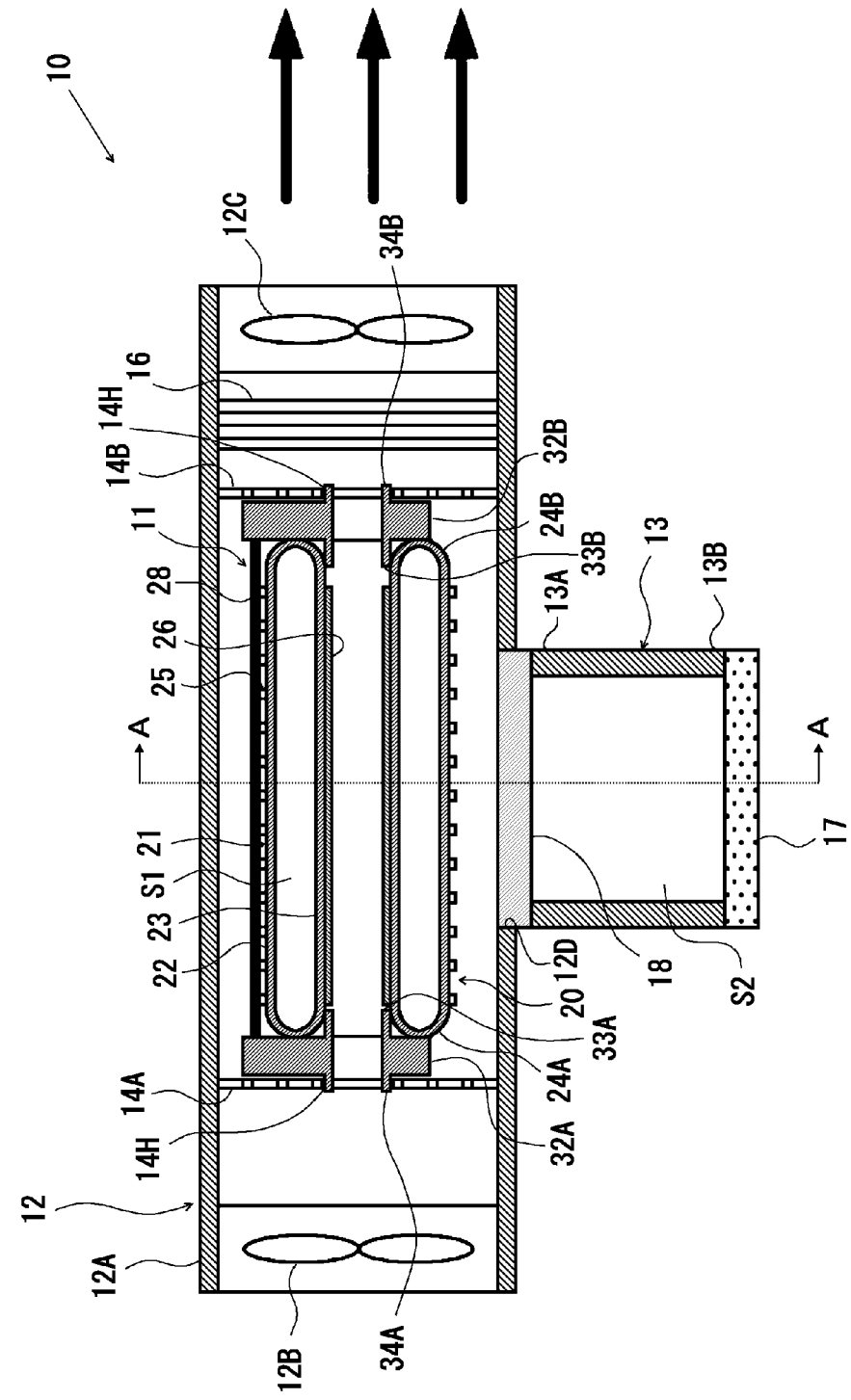
FIG. 1 is an explanatory sectional view illustrating an example of the construction of an ultraviolet sterilizer according to a first embodiment of the present invention.
Figure 2:
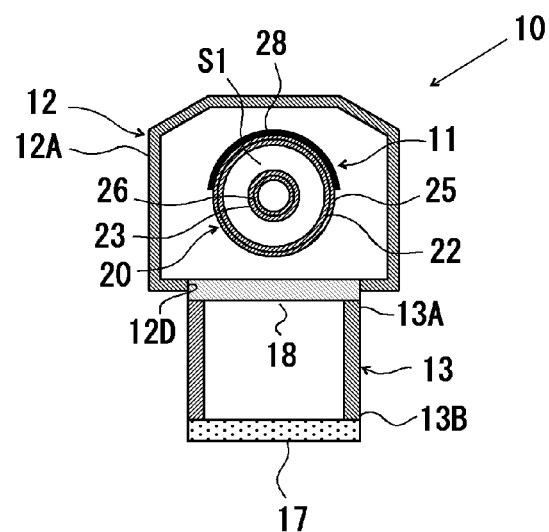
FIG. 2 is a sectional view taken along line A-A in the ultraviolet sterilizer of FIG. 1.
Figure 3:
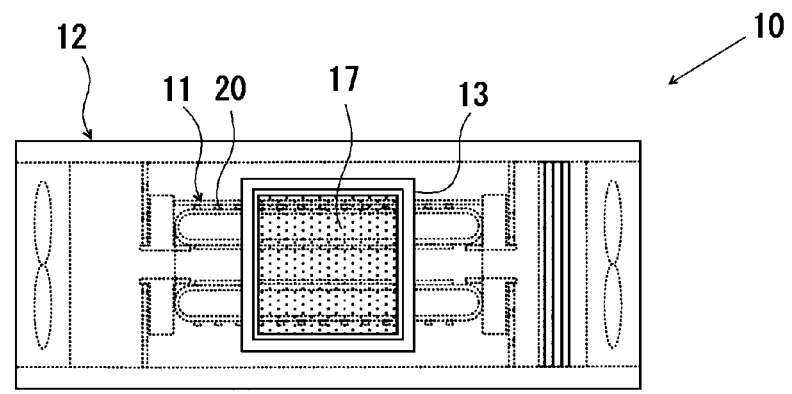
FIG. 3 is a bottom view of the ultraviolet sterilizer of FIG. 1.

Ultraviolet sterilizer of first embodiment: FIG. 1 is an explanatory sectional view illustrating an example of the construction of an ultraviolet sterilizer according to the first embodiment of the present invention. FIG. 2 is a sectional view taken along line A-A in the ultraviolet sterilizer of FIG. 1. FIG. 3 is a bottom view of the ultraviolet sterilizer of FIG. 1.

The ultraviolet sterilizer 10 according to the first embodiment of the present invention includes: an ultraviolet light source unit 11 having an ultraviolet light source for emitting ultraviolet light, including, for example, an excimer lamp 20; a lamp storage chamber 12 for storing the ultraviolet light source unit 11; and a light guiding part 13 including a rectangular cylindrical body for guiding light from the excimer lamp 20.

Ultraviolet Light Source Unit:

The ultraviolet light source unit 11 includes: the ultraviolet light source including the excimer lamp 20 having a straight tubular shape; and a reflective member 28 provided in such a way as to extend along a lamp central axis of the excimer lamp 20.

The reflective member 28 has a total length longer than the total length of the excimer lamp 20. The reflective member 28 is formed from an aluminum concave plane mirror having a rectangular bent plate that is curved in a semicircular shape along a circumferential direction of the excimer lamp 20. The reflective member 28 is disposed in such a way that a reflective surface (an inner peripheral surface) of the reflective member 28 faces the excimer lamp 20. Here, the reflective member 28 may be formed from an aluminum vapor-deposited film provided on an outer peripheral surface of the excimer lamp 20 (specifically, an outer peripheral surface of an outer tube 22 to be described later). An ultraviolet output region is formed by a region of the outer peripheral surface of the outer tube 22 of the excimer lamp 20 that is not faced with the reflective member 28.

The excimer lamp 20 includes a light-emitting tube 21 formed from a dielectric material that transmits ultraviolet light, such as synthetic quartz glass and fused quartz glass, for example. The light-emitting tube 21 has a double-tube structure including: the cylindrical outer tube 22; and a cylindrical inner tube 23 disposed inside the outer tube 22 along its tube axis and having an outer diameter smaller than the inner diameter of the outer tube 22. In this light-emitting tube 21, the outer tube 22 and the inner tube 23 are disposed in such a way that the tube axis of the outer tube 22 coincides with a tube axis of the inner tube 23. These tube axes of the outer tube 22 and the inner tube 23 correspond to the lamp central axis. In the light-emitting tube 21, both ends of each of the outer tube 22 and the inner tube 23 are joined by sealing wall members 24A and 24B, and so an annular internal space S1 is formed between the outer tube 22 and the inner tube 23. A discharge gas is charged in the internal space S1. In the light-emitting tube 21, a net-like outer electrode 25 formed from stainless steel, for example, is provided in close contact with the outer peripheral surface of the outer tube 22. A cylindrical inner electrode 26 formed from aluminum, for example, is provided on an inner peripheral surface of the inner tube 23 in close contact with the inner peripheral surface. Here, the inner electrode 26 may be formed from an aluminum vapor-deposited film provided on the inner peripheral surface of the inner tube 23 in the excimer lamp 20. The pair of electrodes including these outer electrode 25 and inner electrode 26 are disposed facing each other. A tube wall (dielectric material) of the light-emitting tube 21 is interposed between the outer electrode 25 and the internal space S1 and between the inner electrode 26 and the internal space S1. In the internal space S1 of the light-emitting tube 21, a discharge region is formed in a region where the pair of electrodes face each other with the tube wall (dielectric material) of the light-emitting tube 21 and the internal space S1 interposed therebetween.

In the example of this figure, the outer electrode 25 and the inner electrode 26 are each connected to a high-frequency power source (not shown) via a lead (not shown). In order to prevent earth leakage, the outer electrode 25 functions as a ground electrode (low-voltage electrode), and the inner electrode 26 functions as a high-voltage supply electrode.

An excimer lamp having a center wavelength within a wavelength range of 190 to 260 nm, particularly preferably 190 to 250 nm, is preferably used as the excimer lamp 20. Light emitted from the excimer lamp having a center wavelength within a wavelength range of 190 to 260 nm, which is used as the excimer lamp 20, includes effective light (ultraviolet light in a wavelength region of 200 to 230 nm) used for sterilization or medical treatment of the human body as well as harmful light (ultraviolet light in a wavelength region of 230 to 300 nm) harmful to the human body. In addition, the excimer lamp having a center wavelength within a wavelength range of 190 to 260 nm also emits ultraviolet light having a wavelength at which the ultraviolet light generates ozone when absorbed by oxygen (hereinafter, referred to also as "ozone-generating ultraviolet light"). Specifically, the ozone-generating ultraviolet light is ultraviolet light having a wavelength shorter than 190 nm. Since a high concentration of ozone has harmful effects on the human body, ozone generation needs to be prevented from occurring especially when a particular excimer lamp is used in a residential space or the like, specifically when an excimer lamp is used for sterilizing the skin, for example.

As specific examples of the discharge gas used for the excimer lamp 20, may be mentioned an argon fluoride (ArF) gas (the center wavelength of the resultant emitted light is 193 nm), a krypton bromide (KrBr) gas (the center wavelength of the resultant emitted light is 207 nm), a krypton chloride (KrCl) gas (the center wavelength of the resultant emitted light is 222 nm), a krypton fluoride (KrF) gas (the center wavelength of the resultant emitted light is 248 nm), a xenon iodide (XeI) gas (the center wavelength of the resultant emitted light is 253 nm) and a chlorine ($Cl_2$) gas (the center wavelength of the resultant emitted light is 259 nm), for example. Among these, preferably used are an argon fluoride gas, a krypton bromide gas and a krypton chloride gas, more preferably used are a krypton bromide gas and a krypton chloride gas, and most preferably used is a krypton chloride gas.

An ultraviolet excimer fluorescent lamp in which an ultraviolet-emitting fluorescent material having a peak wavelength within a wavelength range of 200 to 250 nm is applied to an inner peripheral surface of the light-emitting tube 21 may be used as the excimer lamp 20. Here, fluorescence from the ultraviolet-emitting fluorescent material has some spectral line width as with the emitted light of the excimer lamp. Thus, light emitted from the ultraviolet excimer fluorescent lamp in which the ultraviolet-emitting fluorescent material having a peak wavelength within a wavelength range of 200 to 250 nm is applied includes effective light (ultraviolet light in a wavelength region of 200 to 230 nm) used for sterilization or medical treatment of the human body as well as harmful light (ultraviolet light in a wavelength region of 230 to 300 nm) harmful to the human body. In addition to light at the peak wavelength, the light emitted from this ultraviolet excimer fluorescent lamp includes light having a longer wavelength than the peak wavelength and light having a shorter wavelength than the center wavelength. Thus, the ultraviolet excimer fluorescent lamp in which the ultraviolet-emitting fluorescent material having a peak wavelength within a wavelength range of 200 to 250 nm is applied also emits light including the ozone-generating ultraviolet light. That is, when the ultraviolet excimer fluorescent lamp is lighted in the atmosphere, the ozone-generating ultraviolet light included in the emitted light of this ultraviolet excimer fluorescent lamp is absorbed by oxygen, thereby generating ozone ($O_3$).

The excimer lamp 20 and the reflective member 28 are supported and fixed by base members 32A and 32B provided at both ends of the excimer lamp 20 and the reflective member 28.

Specifically, the base members 32A and 32B each include a generally annular cylindrical body. A cross section of the generally annular cylindrical body perpendicular to its cylinder axis has a partially-missing circular outer shape without having a part of an annular body having an inner diameter slightly smaller than the inner diameter of the inner tube 23 of the excimer lamp 20 and having an outer diameter slightly larger than the outer diameter of the reflective member 28. The base members 32A and 32B having the generally annular cylindrical shape can cool the excimer lamp 20 with high efficiency by cooling wind introduced into the lamp storage chamber 12 from an air supply fan 12B to be described later. Annular cylindrical engagement parts 33A and 33B, each having an outer diameter slightly smaller than the inner diameter of the inner tube 23 of the excimer lamp 20, protrude from inward-facing surfaces of the base members 32A and 32B (surfaces facing the excimer lamp 20), respectively, in such a state that the insides of the annuli of the engagement parts 33A and 33B are communicated with the insides of the annuli of the base members 32A and 32B. Annular cylindrical engagement parts 34A and 34B protrude from outward-facing surfaces of the base members 32A and 32B, respectively, in such a state that the insides of the annuli of the engagement parts 34A and 34B are communicated with the insides of the annuli of the base members 32A and 32B.

The inward-protruding engagement parts 33A and 33B in the base members 32A and 32B are inserted into the inner tube 23 of the excimer lamp 20, thereby enabling the excimer lamp 20 to be held by the base members 32A and 32B.

Lamp Storage Chamber:

The lamp storage chamber 12 for storing the ultraviolet light source unit 11 includes: a peripheral wall part 12A formed from a generally rectangular cylindrical body; and the air supply fan 12B and an air exhaust fan 12C provided at both ends of the peripheral wall part 12A in a cylinder axis direction thereof for circulating the cooling wind to cool the excimer lamp 20 through the lamp storage chamber 12.

The ultraviolet light source unit 11 is disposed in the lamp storage chamber 12 in such a way that the cylinder axis of the peripheral wall part 12A and the tube axis of the excimer lamp 20 extend coaxially. Specifically, two parts 14A and 14B for supporting the ultraviolet light source unit, each having an outer peripheral shape that is the same as an inner peripheral shape of the peripheral wall part 12A in its cross section perpendicular to its axial direction, are provided spaced apart from each other inside the peripheral wall part 12A of the lamp storage chamber 12. The engagement parts 34A and 34B of the base members 32A and 32B in the ultraviolet light source unit 11 are engaged with engagement holes 14H, 14H provided in the parts 14A and 14B for supporting the ultraviolet light source unit, respectively. This enables the ultraviolet light source unit 11 to be stored in the lamp storage chamber 12 while being supported and fixed by the lamp storage chamber 12.

The peripheral wall part 12A is formed from a material having a light-blocking property, e.g., black alumite aluminum. It is preferable that a reflective layer is provided on a region of an inner surface of the peripheral wall part 12A facing a light-emitting part of the excimer lamp 20.

In the ultraviolet sterilizer 10 of the present invention, a rectangular opening 12D is provided in a region of the peripheral wall part 12A facing the ultraviolet output region of the excimer lamp 20 (specifically, a part of the outer peripheral surface of the outer tube 22 of the excimer lamp 20 opposite to the reflective member 28).

It is preferable that an ozone filter is provided between the excimer lamp 20 and the outside in an air supply passage, which is an air flow passage including the air supply fan 12B, and/or an air exhaust passage, which is an air flow passage including the air exhaust fan 12C.

In the ultraviolet sterilizer 10 in the example of this figure, an ozone filter 16 is provided between the ultraviolet light source unit 11 and the air exhaust fan 12C.

The ozone filter 16 adsorbs and decomposes ozone.

Providing the ozone filter 16 in the air supply passage, which is the air flow passage including the air supply fan 12B, and/or the air exhaust passage, which is the air flow passage including the air exhaust fan 12C, can reduce an amount of ozone generated in the lamp storage chamber 12 and exhausted to the outside of the device.

Band Pass Filter:

In the ultraviolet sterilizer 10 of the first embodiment of the present invention, a band pass filter 18 for reducing harmful light is provided at a position between the light guiding part 13 and the lamp storage chamber 12. Specifically, the band pass filter 18 having an outer peripheral shape that is the same as an inner peripheral shape of the opening 12D, e.g., having a rectangular outer shape, is fitted into, and fixed to, the opening 12D of the peripheral wall part 12A in the lamp storage chamber 12. The light guiding part 13, which includes a rectangular cylindrical body having approximately the same cross-sectional shape as an outer peripheral shape of the band pass filter 18, on the other hand, is disposed in such a way as to protrude from the band pass filter 18 provided in the opening 12D of the lamp storage chamber 12. Specifically, a base end 13A of the light guiding part 13 is fixed to a front surface (a lower surface in FIG. 1) of the band pass filter 18 in such a way that the light guiding part 13 extends in a direction approximately perpendicular to the tube axis of the excimer lamp 20.

For light incident at an angle of at least 0° to 40° (hereinafter, referred to also as "low-angle component light"), the band pass filter 18 blocks, for example, 95% or more of harmful light included in the low-angle component light. Note that this band pass filter 18 hardly blocks harmful light included in light incident at an incidence angle larger than 40° (hereinafter, referred to also as "high-angle component light").

The band pass filter 18 is preferably a band pass filter that causes light having passed through the band pass filter 18 to have a light intensity ratio, represented by the following Formula (1), not higher than 10%. An intensity ratio of light before passing through the band pass filter 18 is about 13%, for example.

light intensity ratio [%]={intensity of harmful light (ultraviolet light in an ultraviolet range having a wavelength region of 230 to 300 nm)/intensity of effective light (ultraviolet light in an effective light range having a wavelength region of 200 to 230 nm)}×100      Formula (1):

Specifically, the intensity ratio of light after having passed through the band pass filter 18 is measured as follows. That is, an optical fiber having a base end to which a uniform diffuser plate (e.g., "CC-3-UV-S" manufactured by Ocean Optics, Inc.) is connected is first set on a rear surface (the surface from which light is outputted) side of the band pass filter 18 in such a way that a base end of the uniform diffuser plate in the optical fiber extends perpendicular to the band pass filter 18 while being spaced apart from the band pass filter 18 by 5 mm. Furthermore, a spectroscope (e.g., "QEpro" manufactured by Ocean Optics, Inc.) is connected to a leading end of the optical fiber. Thereafter, the front surface of the band pass filter 18 is irradiated with light from the excimer lamp 20, and the spectrum of the light after having passed through the band pass filter 18 is measured in the spectroscope. The intensity ratio of the light after having passed through the band pass filter 18 is calculated using an integrated light amount in a wavelength region of 230 to 300 nm in the spectrum as intensity of harmful light and using an integrated light amount in a wavelength region of 200 to 230 nm in the spectrum as intensity of effective light.

Light Guiding Part:

A leading end 13B of the light guiding part 13 for guiding light from the excimer lamp 20 is closed by an irradiation window 17 having an ultraviolet transmitting property.

In the ultraviolet sterilizer 10 of the present invention, an inner surface of the light guiding part 13 is formed from an ultraviolet absorbing member that absorbs harmful light. In the ultraviolet sterilizer 10 of the first embodiment, the light guiding part 13 (rectangular cylindrical body) is composed of an ultraviolet absorbing member that absorbs harmful light.

Ultraviolet Absorbing Member:

The ultraviolet absorbing member may be any member capable of absorbing or transmitting the high-angle component light for the band pass filter 18. Among others, an ultraviolet absorbing member having reflectivity to effective light in a wavelength region of 200 to 230 nm is preferably used.

Glass, such as quartz glass, may be used as the ultraviolet absorbing member.

Glass exhibits the characteristics of Fresnel reflection. Thus, glass reflects light incident thereon at a high angle, while the glass absorbs or transmits light incident thereon at a low angle. Here, the high-angle component light for the band pass filter 18 is incident on the ultraviolet absorbing member at a low angle. Therefore, such high-angle component light is absorbed by, or passes through, the ultraviolet absorbing member. The low-angle component light for the band pass filter 18, on the other hand, is reflected toward the irradiation window 17 by the ultraviolet absorbing member without being absorbed by, or passing through, the ultraviolet absorbing member.

Figure 4:
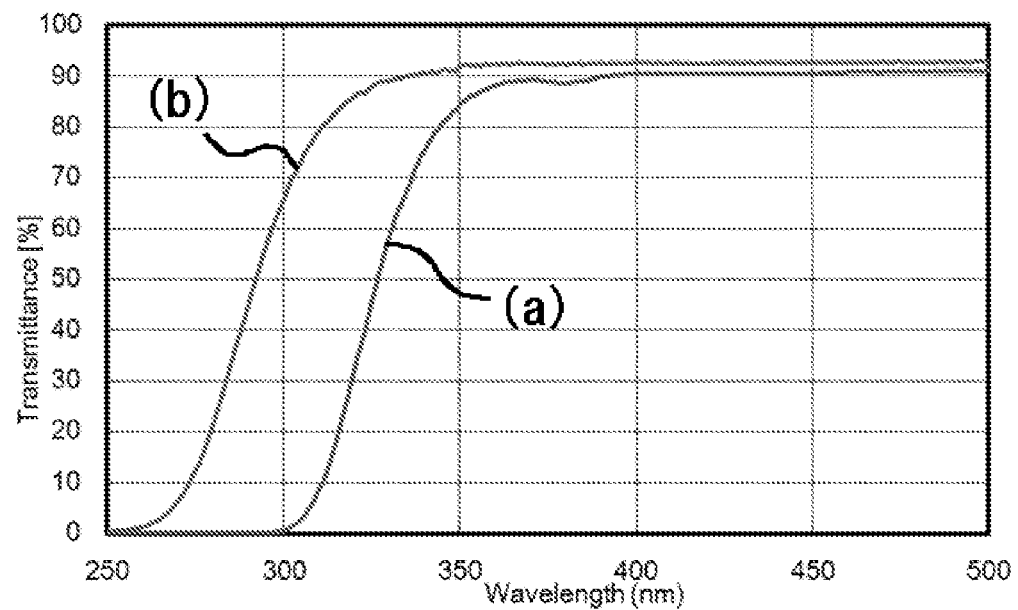
FIG. 4 is a graph showing transmission spectra of soda-lime glass and borosilicate glass.

As alternative examples of glass used as the ultraviolet absorbing member, may be mentioned soda-lime glass and borosilicate glass having transmission spectra as shown in FIG. 4. In FIG. 4, (a) denotes a transmission spectrum of soda-lime glass. Also, (b) denotes a transmission spectrum of borosilicate glass. Since Fresnel reflection is determined by a refractive index of glass, soda-lime glass and borosilicate glass having refractive indexes not much different from a refractive index of quartz glass also exhibit similar Fresnel reflection characteristics.

When soda-lime glass or borosilicate glass is used as the ultraviolet absorbing member, such glass hardly transmits ultraviolet light harmful to the human body. This can reliably prevent the ultraviolet light harmful to the human body from leaking to the outside of the device. According to the ultraviolet sterilizer 10 having the light guiding part 13 using soda-lime glass or borosilicate glass, there is obtained greater convenience because a user can observe visible light of the excimer lamp 20 from the outside.

It is preferable that a space S2 for forming an oxygen-containing layer inside the light guiding part 13, which is partitioned and closed by the band pass filter 18 and the irradiation window 17, is filled with a gas that generates ozone by absorbing ultraviolet light, thereby forming an oxygen-containing layer. The space S2 for forming an oxygen-containing layer may be an airtight closed space without any leakage of ozone generated in the oxygen-containing layer to the outside. However, a high level of airtightness may not be ensured as long as the free flow of the ozone generated in the oxygen-containing layer to the outside is interrupted so as to keep the leakage low.

Any gas containing oxygen may be used as the gas that generates ozone by absorbing ultraviolet light, which fills the space S2 for forming an oxygen-containing layer. Specifically, the atmosphere (air in an environment outside the device) may be used.

A length of the light guiding part 13 may be set to any dimension that can cause all of the high-angle component light for the band pass filter 18, of the light outputted from the band pass filter 18, to be directly incident on the inner surface of the light guiding part 13. Furthermore, when the light guiding part 13 has an oxygen-containing layer formed therein, it is preferable that the length of the light guiding part 13 (the thickness of the oxygen-containing layer) is determined appropriately in consideration of the construction of the excimer lamp 20 (specifically, such as a kind of discharge gas) and lighting conditions of the excimer lamp 20, for example. Specifically, the length of the light guiding part 13 is preferably 10 to 100 mm, more preferably 30 to 60 mm.

As a specific length of the light guiding part 13, the length (length in a vertical direction of FIG. 1) of the light guiding part 13 is, for example, 50 mm when the dimensions of the opening 12D in the lamp storage chamber 12 are, for example, 50 mm×50 mm in height (the length in a direction perpendicular to the paper plane of FIG. 1) and width (the length in a horizontal direction of FIG. 1).

When the light guiding part 13 has an excessively small length, there is a possibility that part of the high-angle component light for the band pass filter 18, of the light outputted from the band pass filter 18, is directly incident on the irradiation window 17 and outputted from the irradiation window 17 without being incident on the inner surface of the light guiding part 13. When the light guiding part 13 has the oxygen-containing layer formed therein, the excessively small length of the light guiding part 13 lowers an ability of absorbing the ozone-generating ultraviolet light in the oxygen-containing layer, thus reducing an amount of ozone generation in the oxygen-containing layer, i.e., an amount of the ozone-generating ultraviolet light absorbed in the oxygen-containing layer. Thus, there is a possibility that ozone generation in the atmosphere outside the device cannot be suppressed sufficiently.

When the light guiding part 13 has an excessively large length, on the other hand, an amount of the low-angle component light for the band pass filter 18, which is the effective light, incident on the ultraviolet absorbing member increases. Thus, there is a possibility that light loss due to the light absorption in the ultraviolet absorbing member increases, thereby reducing an amount of light that can reach the irradiation window 17. When the light guiding part 13 has the oxygen-containing layer formed therein, the excessively large length of the light guiding part 13 enhances a heat retaining action by the oxygen-containing layer. Thus, there is a possibility that the useful life of the excimer lamp 20 is shortened as a result of the excessive heating of the excimer lamp 20 due to, for example, heat generated by the lighting of the excimer lamp 20.

The irradiation window 17 may be formed from a material such as quartz glass.

In this ultraviolet sterilizer 10, a high-frequency high-voltage is applied to the pair of electrodes in the excimer lamp 20 by the high-frequency power source. This generates excimer discharge in the internal space S1, and excimer light in accordance with the kind of discharge gas is emitted from the outer peripheral surface of the outer tube 22 as emitted light. The emitted light from the excimer lamp 20 includes effective light (ultraviolet light in a wavelength region of 200 to 230 nm) used for sterilization or medical treatment of the human body as well as harmful light (ultraviolet light in a wavelength region of 230 to 300 nm) harmful to the human body. The emitted light of the excimer lamp 20, i.e., a part of such light is directly, and the other part of such light, after being reflected by the reflective member 28, is outputted from the ultraviolet output region in the outer peripheral surface of the outer tube 22. The light outputted from the ultraviolet output region in the outer tube 22 of the excimer lamp 20, i.e., a part of such light is directly, and the other part of such light, after being reflected by the inner surface of the peripheral wall part 12A of the lamp storage chamber 12, is incident on the band pass filter 18.

Figure 5:
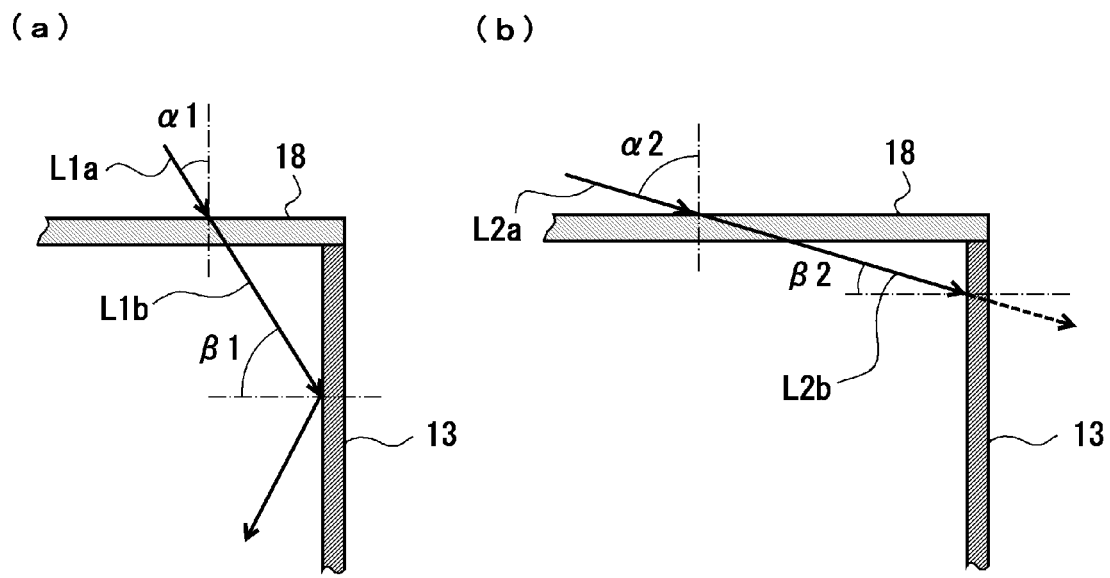
FIG. 5 is a schematic view for explaining transmission of light in a band pass filter and an ultraviolet absorbing member in the ultraviolet sterilizer of the first embodiment.

As shown in FIG. 5(a), of harmful light and effective light included in low-angle component light L1a having been incident on the band pass filter 18 at a low angle α1 of 0° to 40° in the emitted light of the excimer lamp 20 having been incident on the band pass filter 18, the harmful light is selectively absorbed and thereby blocked by the band pass filter 18. The effective light is included in light L1b passing through the band pass filter 18 without being blocked. The light L1b including the effective light, having passed through the band pass filter 18, is directly outputted from the irradiation window 17, or incident on the light guiding part 13 at a high angle β1, reflected by the inner surface of the ultraviolet absorbing member that constitutes the light guiding part 13 and then outputted from the irradiation window 17. As shown in FIG. 5(b), of harmful light and effective light included in high-angle component light L2a having been incident on the band pass filter 18 at a high angle α2 greater than 40° in emitted light of the excimer lamp 20 having been incident on the band pass filter 18, on the other hand, the harmful light is included in light L2b passing through the band pass filter 18. The light L2b including the transmitted harmful light is to be incident on the light guiding part 13 at a low angle β2. Thus, the light L2b including the transmitted harmful light is absorbed and thereby blocked by the ultraviolet absorbing member that constitutes the light guiding part 13, or passes through the ultraviolet absorbing member to be outputted toward a lateral side of the exterior of the light guiding part 13. Note that the effective light included in the high-angle component light L2a is absorbed and thereby blocked by the band pass filter 18. Alternatively, even if having passed through the band pass filter 18 without being blocked, such effective light is absorbed and thereby blocked by the ultraviolet absorbing member or passes through the ultraviolet absorbing member to be outputted toward a lateral side of the exterior of the light guiding part 13 together with the harmful light included in the light L2b.

Thus, the harmful light included in the low-angle component light L1a is blocked by the band pass filter 18 and the effective light is reliably outputted from the irradiation window 17. In addition, the high-angle component light L2a including the harmful light that cannot be completely blocked by the band pass filter 18 is absorbed by or passes through the ultraviolet absorbing member that constitutes the light guiding part 13. This can prevent the high-angle component light L2a including the harmful light from being outputted from the irradiation window 17.

Emitted light from the excimer lamp 20 may include ultraviolet light (ozone-generating ultraviolet light) having a wavelength at which the ultraviolet light generates ozone when absorbed by oxygen. The light having passed through the band pass filter 18, however, enters into the oxygen-containing layer in the light guiding part 13, which is closed by the band pass filter 18 and the irradiation window 17. The ozone-generating ultraviolet light included in such light is selectively absorbed in the oxygen-containing layer, thereby generating ozone. The light from which the ozone-generating ultraviolet light has been eliminated then enters into the irradiation window 17 to be outputted to the outside from the irradiation window 17. Here, the space S2 for forming an oxygen-containing layer, where an oxygen-containing layer is formed, is a closed space. Thus, while ozone is generated as a result of the ozone-generating ultraviolet light being absorbed by oxygen in the atmosphere, such ozone is prevented from leaking to the outside of the device.

As described above, ultraviolet light having reduced emission intensity for the harmful light and the ozone-generating ultraviolet light and having increased emission intensity for the effective light is outputted from the irradiation window 17 of the ultraviolet sterilizer 10.

Activating the air supply fan 12B and the air exhaust fan 12C in the lamp storage chamber 12 causes the atmosphere outside the device to flow, as the cooling wind, from one end side where the air supply fan 12B is disposed toward the other end side where the air exhaust fan 12C is disposed.

The light outputted from the ultraviolet output region of the outer tube 22 in the excimer lamp 20 is absorbed also in an oxygen-containing layer (air layer) in the lamp storage chamber 12, thereby generating ozone. Such ozone is heated and immediately decomposed (thermal decomposition), for example, by heat from the excimer lamp 20, thereby generating oxygen, or adsorbed and thereby removed by the ozone filter 16 provided between the excimer lamp 20 and the air exhaust fan 12C. Thus, an amount of ozone to be exhausted to the outside of the device can be reduced.

Thus, according to the ultraviolet sterilizer 10, ozone generation in the atmosphere outside the device can be reduced, and selectively using a discharge gas in the excimer lamp 20 enables ultraviolet light in a desired wavelength range around a wavelength of 200 nm to be emitted with high emission intensity. Furthermore, even when the ultraviolet sterilizer 10 generates ozone therein, such ozone can be prevented from leaking to the outside of the device.

Such an ultraviolet sterilizer of the present invention can be preferably used, for example, as an ultraviolet sterilizer for the skin, which utilizes ultraviolet light in a wavelength region of 200 to 230 nm, for example.

In the above-described ultraviolet sterilizer 10 of the first embodiment, the band pass filter 18 for reducing harmful light is provided between the light guiding part 13 and the lamp storage chamber 12, and the inner surface of the light guiding part 13 is formed from the ultraviolet absorbing member that absorbs harmful light. Thus, part of harmful light included in light from the excimer lamp 20 is selectively blocked by the band pass filter 18, and the remaining part of the harmful light is absorbed by, or passes through, the ultraviolet absorbing member. Furthermore, of effective light included in light from the excimer lamp 20, the light having been incident on the ultraviolet absorbing member is reflected by the ultraviolet absorbing member and outputted from the irradiation window. As a result, in light outputted from the ultraviolet sterilizer 10, emission intensity of harmful light can be reduced without significantly reducing emission intensity of ultraviolet light including effective light.

In the above-described ultraviolet sterilizer 10 including the oxygen-containing layer formed in the space S2 for forming an oxygen-containing layer in the light guiding part 13, light from the excimer lamp 20 that emits light including ozone-generating ultraviolet light is outputted via the oxygen-containing layer. Thus, the ozone-generating ultraviolet light included in the light from the excimer lamp 20 is selectively absorbed in this oxygen-containing layer. As a result, in the light outputted from this ultraviolet sterilizer 10, emission intensity of ozone-generating ultraviolet light can be reduced without significantly reducing emission intensity of ultraviolet light excluding the ozone-generating ultraviolet light.

Thus, according to this ultraviolet sterilizer 10, ozone generation in the atmosphere outside the device can be reduced, and ultraviolet light around a wavelength of 200 nm can be emitted with high emission intensity.

The ozone-generating ultraviolet light included in the light from the excimer lamp 20 is absorbed by the atmosphere in the lamp storage chamber 12, thereby generating ozone. Due to the provision of the ozone filter 16, however, such ozone is adsorbed by the ozone filter 16. As a result, an amount of ozone to be exhausted to the outside of the device can be reduced.

Figure 6:
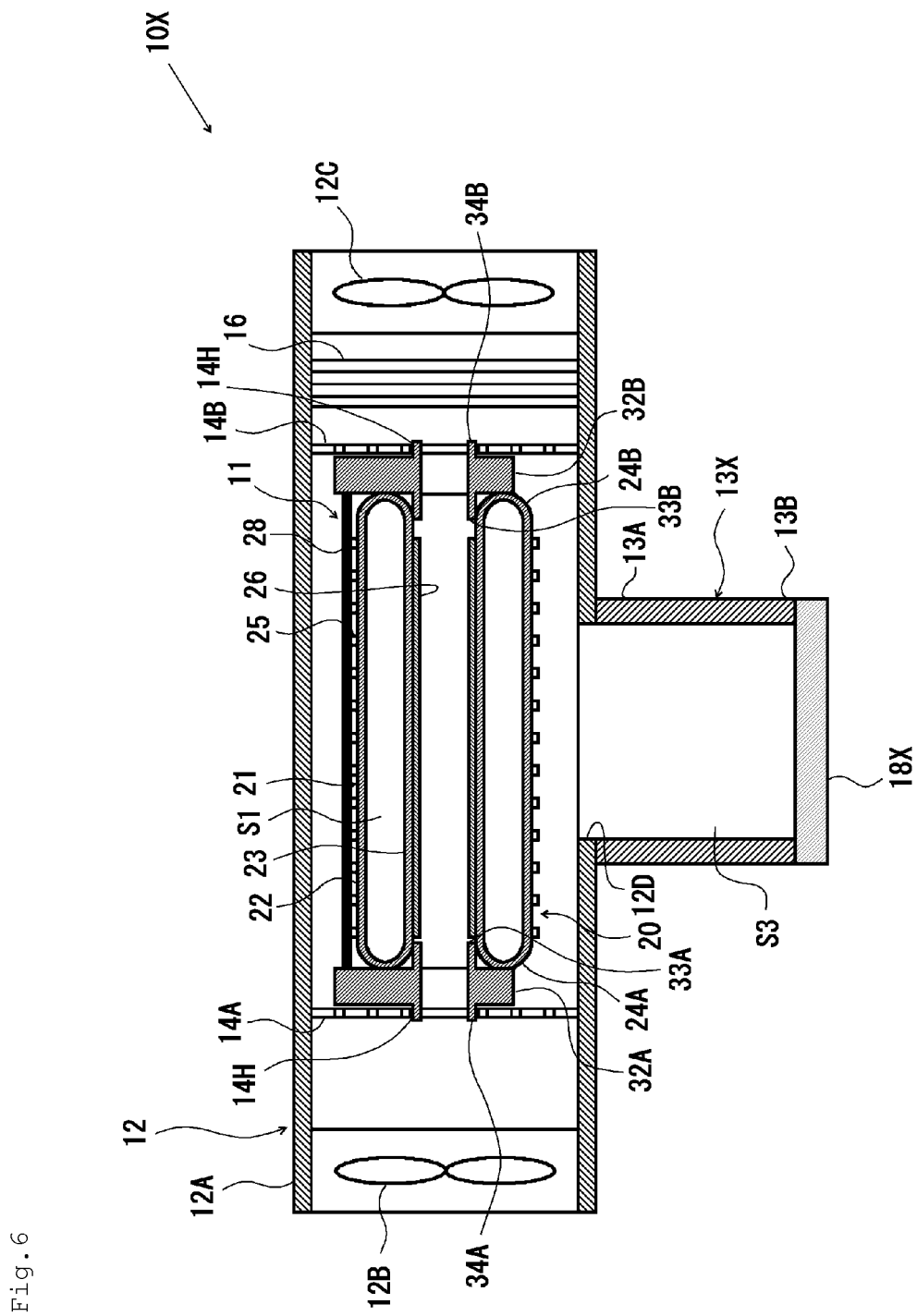
FIG. 6 is an explanatory sectional view illustrating an example of the construction of an ultraviolet sterilizer according to a second embodiment of the present invention.

Ultraviolet Sterilizer of Second Embodiment:

FIG. 6 is an explanatory sectional view illustrating an example of the construction of an ultraviolet sterilizer according to the second embodiment of the present invention.

An ultraviolet sterilizer 10X according to the second embodiment of the present invention has the same construction as that of the ultraviolet sterilizer 10 of the first embodiment except that no band pass filter 18 is provided, a band pass filter 18X is provided, instead of the irradiation window 17, and the band pass filter 18X functions as an irradiation window. In FIG. 6, the same components as those of the ultraviolet sterilizer 10 of the first embodiment in FIG. 1 are denoted by the same reference numerals.

Specifically, the ultraviolet sterilizer 10X of the second embodiment includes the band pass filter 18X for reducing harmful light at a position of a light outputting leading end 13B of a light guiding part 13X.

The light guiding part 13X may have any length as long as light directly incident on the band pass filter 18X, of emitted light from an excimer lamp 20, has an incidence angle of 0 to 40°.

When the light guiding part 13X has an excessively small length, the emitted light directly traveling from the excimer lamp 20 toward the band pass filter 18X includes high-angle component light for which an incidence angle to the band pass filter 18X is larger than 40°. Thus, there is a possibility that harmful light included in the high-angle component light is outputted from the band pass filter 18X without being absorbed and thereby removed by the band pass filter 18X.

When the light guiding part 13X has an excessively large length, on the other hand, the low-angle component light having an incidence angle to the band pass filter 18X that is not higher than 40° also enters into an inner surface of the light guiding part 13X, is absorbed by or passes through an ultraviolet absorbing member that constitutes the light guiding part 13X. Thus, there is a possibility that utilization efficiency of effective light in the emitted light from the excimer lamp 20 is deteriorated.

In the ultraviolet sterilizer 10X, it is preferable that a space S3 for forming an oxygen-containing layer, which is formed by the interior of the light guiding part 13X, is filled with a gas that absorbs ultraviolet light and thereby generates ozone so as to form an oxygen-containing layer. The space S3 for forming an oxygen-containing layer is an open space open to the inside of a lamp storage chamber 12. Even when the space S3 for forming an oxygen-containing layer is the open space open to the inside of the lamp storage chamber 12, the oxygen-containing layer is heated by heat from an ultraviolet light source, or the like, to have high temperature. In addition, the atmosphere that constitutes the oxygen-containing layer is less likely to flow. Thus, ozone generated in the oxygen-containing layer is immediately decomposed (thermal decomposition), or adsorbed and thereby removed by an ozone filter 16 provided between the ultraviolet light source and an air exhaust fan 12C. This can reduce an amount of ozone to be exhausted to the outside of the device.

The gas that absorbs ultraviolet light and thereby generates ozone, which fills the space S3 for forming an oxygen-containing layer, is the atmosphere (air in an environment outside the device).

Figure 7:
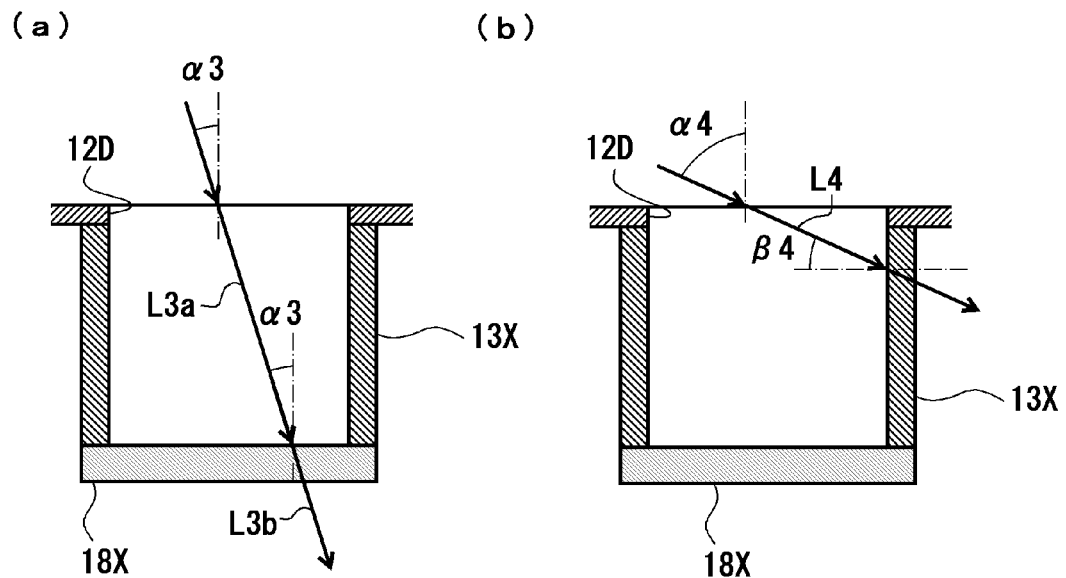
FIG. 7 is a schematic view for explaining transmission of light in a band pass filter and an ultraviolet absorbing member in the ultraviolet sterilizer of the second embodiment.

In this ultraviolet sterilizer 10X, light incident at a low angle α3 corresponding to an incidence angle not higher than 40°, of emitted light of the excimer lamp 20 having entered into an opening 12D of the lamp storage chamber 12, is also incident on the band pass filter 18X at the low angle α3 not higher than 40° as shown in FIG. 7 (a). Of harmful light and effective light included in low-angle component light L1a having been incident on the band pass filter 18X, the harmful light is selectively absorbed and thereby blocked by the band pass filter 18X. Light L3b including the effective light passes through the band pass filter 18X, without being blocked, to be outputted from the band pass filter 18X. As shown in FIG. 7 (b), high-angle component light L4 incident at a high angle α4 corresponding to an incidence angle larger than 40°, on the other hand, of the emitted light of the excimer lamp 20 having entered into the opening 12D of the lamp storage chamber 12, directly enters into the ultraviolet absorbing member that constitutes the light guiding part 13X. The high-angle component light L4 having been incident on the ultraviolet absorbing member is to be incident on the inner surface of the light guiding part 13X at a low angle β4. Thus, the high-angle component light L4 including both effective light and harmful light is absorbed and thereby blocked by the ultraviolet absorbing member that constitutes the light guiding part 13X, or passes through the ultraviolet absorbing member to be outputted toward a lateral side of the exterior of the light guiding part 13X, i.e., not outputted from the band pass filter 18X.

Thus, the harmful light included in the low-angle component light L3a is blocked by the band pass filter 18X, and the effective light included in the low-angle component light L3a is reliably outputted from the band pass filter 18X. In addition, the high-angle component light L4 having entered into the opening 12D of the lamp storage chamber 12 at a high angle is absorbed by, or passes through, the ultraviolet absorbing member that constitutes the light guiding part 13X, thus preventing the high-angle component light L4 including the harmful light from being incident on the band pass filter 18X at a high angle. Thus, the harmful light can be prevented from being outputted from the band pass filter 18X.

Emitted light from the excimer lamp 20 may include ultraviolet light (ozone-generating ultraviolet light) having a wavelength at which the ultraviolet light generates ozone when absorbed by oxygen. The light having entered into the light guiding part 13X, however, enters into the oxygen-containing layer, which is formed by the interior of the light guiding part 13X. The ozone-generating ultraviolet light included in such light is selectively absorbed in the oxygen-containing layer, thereby generating ozone. The light from which the ozone-generating ultraviolet light has been eliminated then enters into the band pass filter 18X to be outputted to the outside from the band pass filter 18X.

As described above, ultraviolet light having reduced emission intensity for the harmful light and the ozone-generating ultraviolet light and having increased emission intensity for the effective light around a wavelength of 200 nm is outputted from the band pass filter 18X of the ultraviolet sterilizer 10X.

In the above-described ultraviolet sterilizer 10X of the second embodiment, the band pass filter 18X for reducing harmful light is provided at the light outputting leading end of the light guiding part 13X, and the inner surface of the light guiding part 13X is formed from the ultraviolet absorbing member that absorbs harmful light. Thus, part of harmful light included in light from the excimer lamp 20 is absorbed by, or passes through, the ultraviolet absorbing member, and the remaining part of the harmful light is selectively blocked by the band pass filter 18X. Thus, in light outputted from the ultraviolet sterilizer 10X, emission intensity of harmful light can be reduced without significantly reducing emission intensity of ultraviolet light including effective light.

While the embodiments of the present invention have been described above, the present invention is not limited to the above-described embodiments and various modifications can be added thereto.

Figure 8:
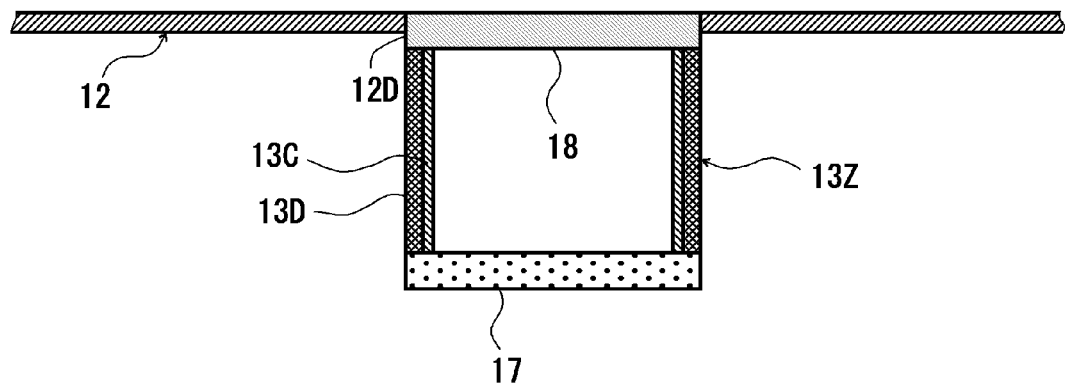
FIG. 8 is a partial sectional view illustrating another example of the construction of the ultraviolet sterilizer of the present invention.

For example, it is only necessary that an inner surface of a light guiding part is composed of an ultraviolet absorbing member that absorbs harmful light. As shown in FIG. 8, the light guiding part may be a light guiding part 13Z in which an ultraviolet absorbing member layer 13C is formed on an inner surface of a rectangular cylindrical outer shell 13D. The ultraviolet absorbing member layer 13C may be formed from glass as mentioned above, or a black layer made of black alumite or black paint. In FIG. 8, the same components as those of the ultraviolet sterilizer in FIG. 1 are denoted by the same reference numerals.

Figure 9:
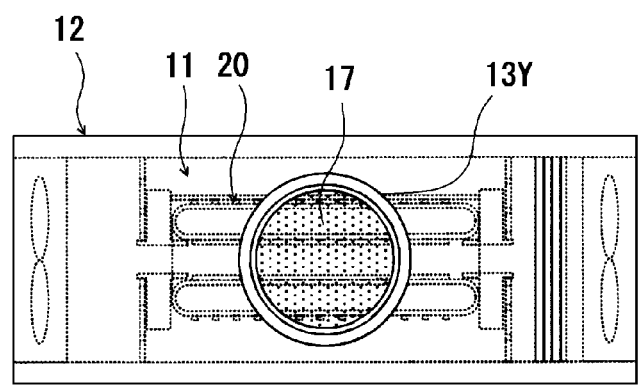
FIG. 9 is a bottom view illustrating still another example of the construction of the ultraviolet sterilizer of the present invention.
Figure 10:
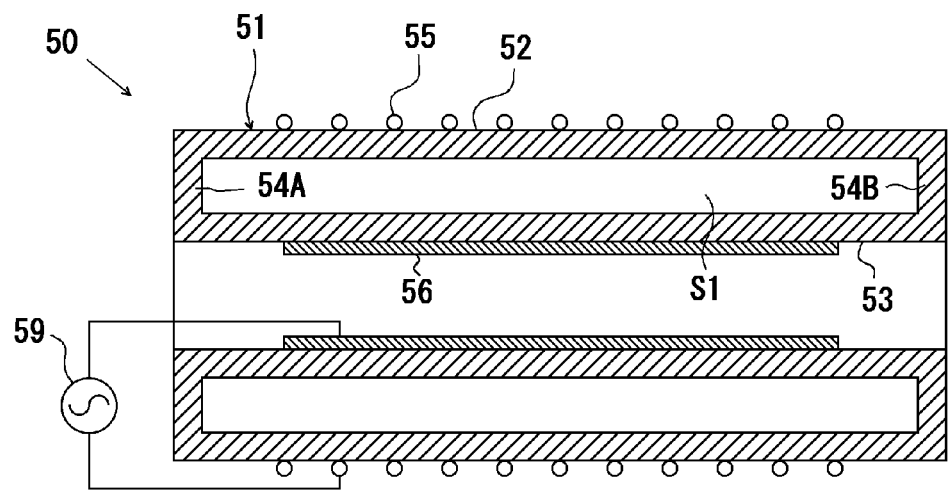
FIG. 10 is an explanatory sectional view illustrating an example of the construction of an excimer lamp.

For example, the shape of the light guiding part is not limited to the rectangular cylindrical shape, but may be a cylindrical light guiding part 13Y as shown in FIG. 9. In FIG. 9, the same components as those of the ultraviolet sterilizer in FIG. 1 are denoted by the same reference numerals.

For example, an ultraviolet light source may be configured such that an excimer lamp is provided in a mantle tube.

For example, the ultraviolet light source is not limited to the excimer lamp including the light-emitting tube having the above-described double-tube structure. An excimer lamp including a light-emitting tube of a single-tube type, such as a flat tube, may be used instead.

For example, an ozone decomposition unit may be disposed in the space for forming an oxygen-containing layer in the light guiding part. A device for thermally decomposing ozone generated in the oxygen-containing layer, specifically, a heater, for example, may be used as the ozone decomposition unit.

EXAMPLES

While specific examples of the present invention will be described below, the present invention is not limited to the following examples.

Example 1

An ultraviolet sterilizer (hereinafter, referred to also as an "ultraviolet sterilizer [1]") having the construction shown in FIG. 1 was produced.

The produced ultraviolet sterilizer [1] has the following specifications.

Figure 11:
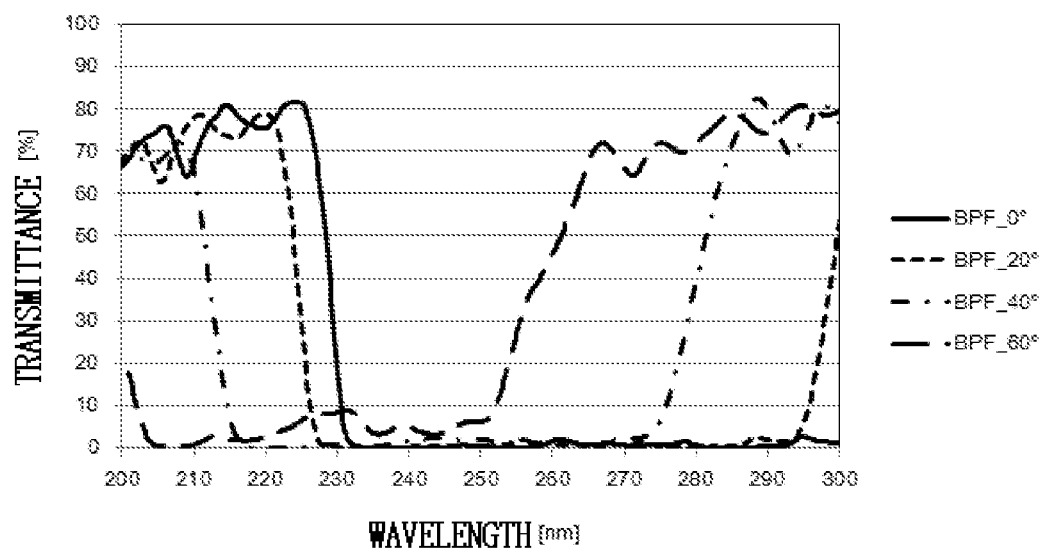
FIG. 11 is a graph for explaining incidence angle dependence of light transmittance in a band pass filter.

Excimer Lamp:
Outer tube: material; synthetic quartz glass, outer diameter; 40 mm, inner diameter; 36 mm
Inner tube: material; synthetic quartz glass, outer diameter; 26 mm, inner diameter; 24 mm
Discharge gas: kind (kind of charged gas); a mixed gas (total charged pressure; 20.1 kPa (151 Torr)) of krypton (charged pressure; 20 kPa (150 Torr)) and chlorine (charged pressure; 133 Pa (1 Torr))
Emitted ultraviolet light: light centered around an emission wavelength of 222 nm
Lamp total length: 100 mm
Distance of discharge space: 5 mm
Lamp Storage Chamber:
Peripheral wall part: material; aluminum, width (length in the direction perpendicular to the paper plane of FIG. 1); 50 mm, height (length in the vertical direction of FIG. 1); 50 mm, total length; 130 mm, opening dimensions; 50 mm×50 mm
Band Pass Filter:
Angular characteristics; having incidence angle dependence of filter transmittance shown in a spectrum of FIG. 11
Light Guiding Part:
Material; quartz glass, height (length in the direction perpendicular to the paper plane of FIG. 1); 50 mm, width (length in the horizontal direction of FIG. 1); 50 mm, length (length in the vertical direction of FIG. 1); 50 mm Irradiation window:
Material; quartz glass, height (length in the direction perpendicular to the paper plane of FIG. 1); 50 mm, width (length in the horizontal direction of FIG. 1); 50 mm, thickness; 2 mm For the produced ultraviolet sterilizer [1], the spectrum of the produced ultraviolet sterilizer [1] was measured during its operation in which the air supply fan and the air exhaust fan were rotated and the excimer lamp was lighted. An illuminance of ultraviolet light having a wavelength of 200 to 230 nm and an intensity ratio of harmful light were calculated. The results are shown in the following Table 1. The spectrum was measured with "QEPro" (manufactured by Ocean Optics, Inc.).

The intensity ratio of harmful light as used herein refers to a ratio between the integral value of light intensity in a wavelength region of 230 to 300 nm and the integral value of light intensity in a wavelength region of 200 to 230 nm in the spectrum. A larger intensity ratio of harmful light indicates larger light intensity in a wavelength region of 230 to 300 nm, i.e., a larger amount of harmful light.

Example 2

An ultraviolet sterilizer [2] having the same construction as that of the ultraviolet sterilizer [1] according to Example 1 except that a black paint layer was formed on an inner surface of a rectangular cylindrical outer shell as a light guiding part was produced.

For the ultraviolet sterilizer [2], its spectrum during the operation of the excimer lamp was measured with the same technique as that in Example 1, and an illuminance of ultraviolet light having a wavelength of 200 to 230 nm and an intensity ratio of harmful light were calculated. The results are shown in the following Table 1.

Comparative Example 1

An ultraviolet sterilizer [3] having the same construction as that of the ultraviolet sterilizer [1] of Example 1 except that an aluminum reflective layer was formed on an inner surface of a rectangular cylindrical outer shell as a light guiding part was produced.

For the ultraviolet sterilizer [3], its spectrum during the operation of the excimer lamp was measured with the same technique as that in Example 1, and an illuminance of ultraviolet light having a wavelength of 200 to 230 nm and an intensity ratio of harmful light were calculated. The results are shown in the following Table 1.

TABLE 1

| | DEVICE NO. | ILLUMINANCE OF ULTRA- VIOLET LIGHT | INTENSITY RATIO OF HARMFUL LIGHT |
|---|---|---|---|
| EXAMPLE 1 | [1] | 1 | 1 |
| EXAMPLE 2 | [2] | 0.8 | 0.8 |
| COMPARATIVE EXAMPLE 1 | [3] | 1.2 | 3.7 |

In Table 1, as the illuminances of ultraviolet light and the intensity ratios of harmful light in the ultraviolet sterilizers [1] to [3], the illuminances of ultraviolet light and the intensity ratios of harmful light during the operations of the ultraviolet sterilizers [1] to [3] are shown with the illuminance of ultraviolet light and the intensity ratio of harmful light in the ultraviolet sterilizer [1] being set to 1 as a reference.

On the basis of the results of Table 1, it has been confirmed that the ultraviolet sterilizer [1] according to Example 1 of the present invention can remove harmful light while obtaining sufficiently large emission intensity for effective light.

Also, it has been confirmed that the ultraviolet sterilizer [2] according to Example 2 of the present invention can reliably remove harmful light although its emission intensity for effective light is rather reduced as compared to Example 1. The reason for this is believed that, in the case of the quartz glass light guiding part, reflected effective light was absorbed by the black paint layer.

Also, it has been found out that the ultraviolet sterilizer [3] according to Comparative Example 1 has difficulty in removing harmful light although large emission intensity for effective light can be obtained. The reason for this is believed that the harmful light included in the high-angle component light for the band pass filter passed through the band pass filter, was directly reflected by the inner surface of the light guiding part due to the aluminum reflective layer of the light guiding part, and outputted from the irradiation window together with the effective light.

Experimental Example 1 for Ozone Concentrations

Figure 12:
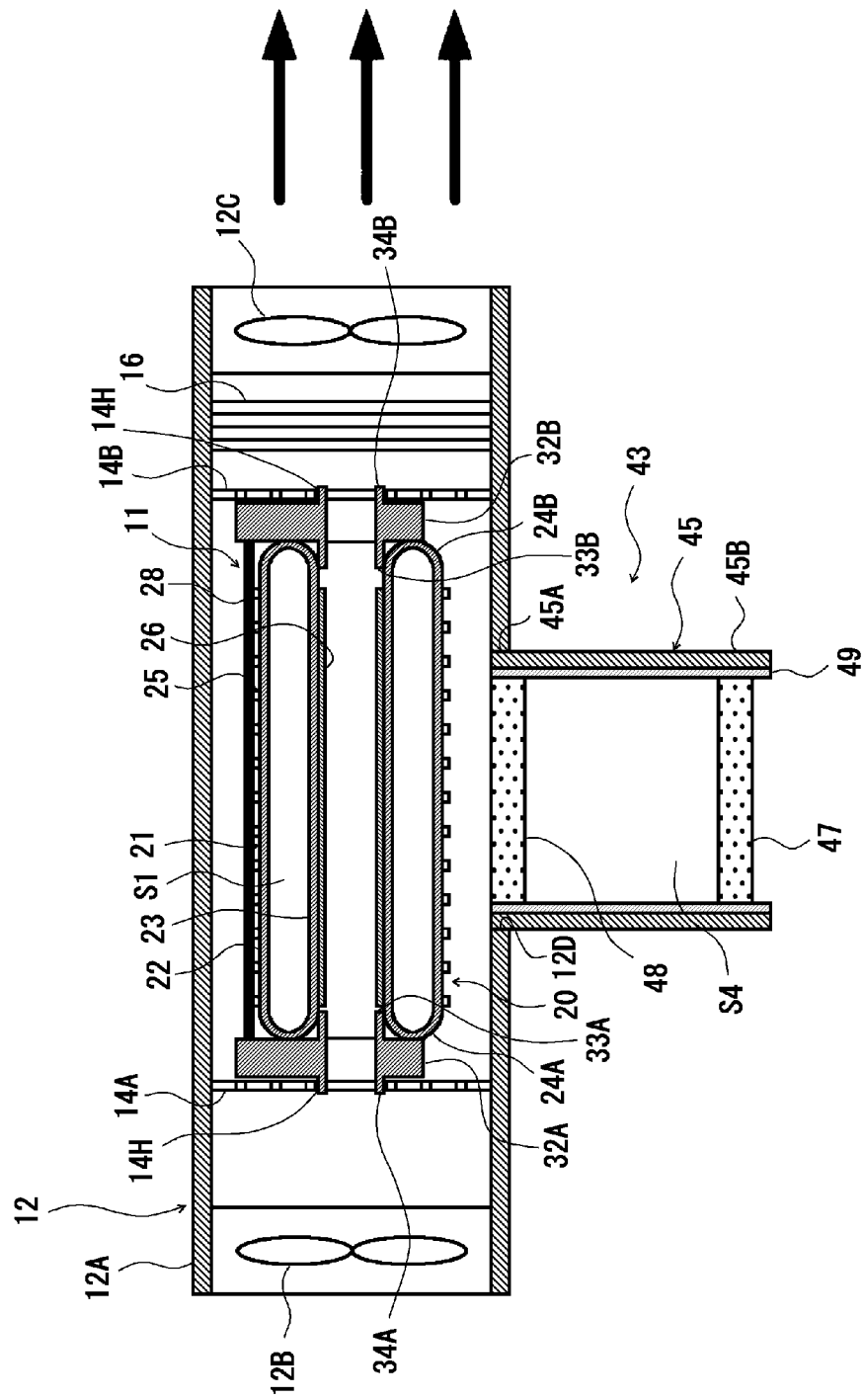
FIG. 12 is an explanatory sectional view illustrating the construction of an ultraviolet emitting device used in an experimental example.

An ultraviolet emitting device for experiments on ozone concentrations (hereinafter, referred to also as an "ultraviolet emitting device [1]"), which has the construction shown in FIG. 12, was produced. The ultraviolet emitting device having the construction shown in FIG. 12 has the same construction as that of the ultraviolet sterilizer having the construction shown in FIG. 1 except that a light guiding part 43 for experiments on ozone concentrations is attached in place of the band pass filter 18, the light guiding part 13 and the irradiation window 17.

Specifically, the light guiding part 43 for experiments on ozone concentrations includes a cylindrical part 45 having a rectangular cylindrical shape. A light guiding window 48 having an outer peripheral shape that is the same as an inner peripheral shape of a base end 45A of the cylindrical part 45 and having an ultraviolet transmitting property is fitted into, and fixed to, the base end 45A. A leading end 45B of the cylindrical part 45, on the other hand, is closed by an irradiation window 47 having an ultraviolet transmitting property. Specifically, the irradiation window 47 having an outer peripheral shape that is the same as an inner peripheral shape of the leading end 45B is fitted into, and fixed to, the leading end 45B of the cylindrical part 45.

A reflective layer 49 including a bright aluminum plate or an aluminum vapor-deposited film, for example, for reflecting light from an exciter lamp 20 is provided on an inner peripheral surface of the cylindrical part 45.

A space S4 for forming an oxygen-containing layer, which is partitioned by the reflective layer 49 provided on the inner peripheral surface of the cylindrical part 45, the light guiding window 48 and the irradiation window 47 in the light guiding part 43, is filled with a gas that generates ozone by absorbing ultraviolet light, thereby forming an oxygen-containing layer.

The light guiding part 43 is disposed in such a way as to protrude from a lamp storage chamber 12. Specifically, the base end 45A of the cylindrical part 45 in the light guiding part 43 is fitted into, and fixed to, an opening 12D of a peripheral wall part 12A of the lamp storage chamber 12 in such a state that the cylindrical part 45 of the light guiding part 43 extends in a direction perpendicular to the tube axis of the excimer lamp 20.

The produced ultraviolet emitting device [1] has the following specifications.

Excimer Lamp:
 Outer tube: material; synthetic quartz glass, outer diameter; 40 mm, inner diameter; 36 mm
 Inner tube: material; synthetic quartz glass, outer diameter; 26 mm, inner diameter; 24 mm
 Discharge gas: kind (kind of charged gas); a mixed gas (total charged pressure; 20.1 kPa (151 Torr)) of krypton (charged pressure; 20 kPa (150 Torr)) and chlorine (charged pressure; 133 Pa (1 Torr))
 Emitted ultraviolet light: light centered around an emission wavelength of 222 nm
 Lamp total length: 100 mm
 Distance of discharge space: 5 mm
Lamp Storage Chamber:
 Peripheral wall part: material; aluminum, width (length in the direction perpendicular to the paper plane of FIG. 12); 50 mm, height (length in the vertical direction of FIG. 12); 50 mm, total length; 130 mm Light guiding part:
 Light guiding window: material; quartz glass, height (length in the direction perpendicular to the paper plane of FIG. 12); 50 mm, width (length in the horizontal direction of FIG. 12); 50 mm, thickness; 1.3 mm Irradiation window: material; quartz glass, height (length in the direction perpendicular to the paper plane of FIG. 12); 50 mm, width (length in the horizontal direction of FIG. 12); 50 mm, thickness; 1 mm Oxygen-containing layer: thickness (length in the vertical direction of FIG. 12); 40 mm For the produced ultraviolet emitting device [1], maximum ozone concentrations in the vicinity of the irradiation window and in the vicinity of the air exhaust fan in the atmosphere outside the device were measured during its operation in which the air supply fan and the air exhaust fan were rotated and the excimer lamp was lighted. The results are shown in the following Table 2. The ozone concentrations were measured with an ozone concentration meter "EG-3000F" (manufactured by EBARA JITSUGYO, CO., LTD.).

Experimental Example 2 for Ozone Concentrations

An ultraviolet emitting device [2] having the same construction as that of the ultraviolet emitting device [1] according to Experimental Example 1 except that no light guiding window was provided was produced.

For the ultraviolet emitting device [2], ozone concentrations in the atmosphere outside the device were measured during the operation of the excimer lamp with the same technique as that in Experimental Example 1. The results are shown in the following Table 2.

Comparative Experimental Example 1 for Ozone Concentrations

An ultraviolet emitting device [3] having the same construction as that of the ultraviolet emitting device [1] according to Experimental Example 1 except that no light guiding part interposed between a light guiding window and an irradiation window was provided, and an irradiation window was directly fitted into an opening of a lamp storage chamber was produced.

For the ultraviolet emitting device [3], ozone concentrations in the atmosphere outside the device were measured during the operation of the excimer lamp with the same technique as Experimental Example 1. The results are shown in the following Table 2.

TABLE 2

| | | OZONE CONCENTRATIONS [ARBITRARY UNIT] | |
| --- | --- | --- | --- |
| | DEVICE NO. | NEAR AIR EXHAUST FAN | NEAR IRRADIATION WINDOW |
| EXPERIMENTAL EXAMPLE 1 | [1] | 1 | 1 |
| EXPERIMENTAL EXAMPLE 2 | [2] | 1.3 | 1 |
| COMPARATIVE EXPERIMENTAL EXAMPLE 1 | [3] | 1 | 2 |

In Table 2, as the ozone concentrations in the ultraviolet emitting devices [1] to [3], relative values of ozone concentrations in the atmosphere outside the devices during the operations of the ultraviolet emitting devices [1] to [3] are shown with the ozone concentration in the atmosphere outside the device in the vicinity of the irradiation window outside the ultraviolet emitting device [1] being set to 1 as a reference.

On the basis of the results of Table 2, it has been confirmed that the ultraviolet emitting device [1] according to Experimental Example 1 can highly suppress ozone generation in the atmosphere outside the device.

Also, it has been confirmed that the ultraviolet emitting device [2] according to Experimental Example 2 can highly suppress ozone generation in the vicinity of the irradiation window outside the device. The reason for this is believed that ozone generation by light emitted from the irradiation window was suppressed as a result of the ozone-generating ultraviolet light sufficiently absorbed in the oxygen-containing layer. It has been also confirmed that the ozone concentration in the vicinity of the air exhaust fan can be kept low to some extent. The reason for this is believed that only a part of ozone generated in the space for forming an oxygen-containing layer, which was open to the lamp storage chamber, left undecomposed by heat from the excimer lamp was exhausted by the air exhaust fan.

Also, it has been found out that the ozone concentration is high in the vicinity of the irradiation window in the ultraviolet emitting device [3] according to Comparative Experimental Example 1. The reason for this is believed that the excessively small interval between the excimer lamp and the irradiation window failed to obtain a sufficient thickness of the oxygen-containing layer, and thus the ozone-generating ultraviolet light was emitted to the outside of the device without being absorbed sufficiently.

REFERENCE SIGNS LIST 10, 10X ultraviolet sterilizer
11 ultraviolet light source unit
12 lamp storage chamber
12A peripheral wall part
12B air supply fan
12C air exhaust fan
12D opening
13, 13X, 13Y, 13Z light guiding part
13A base end
13B leading end
13C ultraviolet absorbing member layer
13D outer shell
14A, 14B part for supporting ultraviolet light source unit
14H engagement hole
16 ozone filter
17 irradiation window
18, 18X band pass filter
20 excimer lamp
21 light-emitting tube
22 outer tube
23 inner tube
24A, 24B sealing wall member
25 outer electrode
26 inner electrode
28 reflective member
32A, 32B base member
33A, 33B engagement part
34A, 34B engagement part
43 light guiding part
45 cylindrical part
45A base end
45B leading end
47 irradiation window
48 light guiding window
49 reflective layer
50 excimer lamp
51 light-emitting tube 52 outer tube
53 inner tube
54A, 54B sealing wall member
55 outer electrode
56 inner electrode
59 high-frequency power source
S1 internal space
S2, S3, S4 space for forming oxygen-containing layer

The invention claimed is:

1. An ultraviolet sterilizer comprising:
an ultraviolet light source;
a lamp storage chamber for storing the ultraviolet light source; and
a light guiding part for guiding light from the ultraviolet light source, wherein
the light guiding part which includes a cylindrical body is disposed so as to protrude in a direction approximately perpendicular to a tube axis of the ultraviolet light source from an opening provided in a peripheral wall part of the lamp storage chamber,
a band pass filter for reducing ultraviolet light in a wavelength region of 230 to 300 nm which is harmful to a human body is provided at least one of a position between the light guiding part and the lamp storage chamber and a position of a light outputting leading end of the light guiding part, and
an inner surface of the light guiding part is formed from an ultraviolet absorbing member that absorbs the ultraviolet light in the wavelength region of 230 to 300 nm which is harmful to the human body.

2. The ultraviolet sterilizer according to claim 1, wherein the band pass filter is a band pass filter that makes a light intensity ratio represented by the following Formula (1) not higher than 10%, light intensity ratio [%]={(intensity in an ultraviolet range having a wavelength region of 230 to 300 nm harmful to the human body)/(intensity in an effective light range having a wavelength region of 200 to 230 nm)}×100.  Formula (1):

3. The ultraviolet sterilizer according to claim 1, wherein effective light in a wavelength region of 200 to 230 nm that has passed through the band pass filter is reflected by the ultraviolet absorbing member.

4. The ultraviolet sterilizer according to claim 1, wherein the ultraviolet absorbing member is composed of glass.

5. The ultraviolet sterilizer according to claim 1, wherein the ultraviolet light source is an excimer lamp having a center wavelength within a wavelength range of 190 to 260 nm.

6. The ultraviolet sterilizer according to claim 1, wherein the light guiding part has a cylindrical body, the band pass filter or an irradiation window having an ultraviolet transmitting property is provided at a leading end of the cylindrical body, and an oxygen-containing layer is formed in the cylindrical body, and
ultraviolet light having a wavelength at which the ultraviolet light generates ozone when absorbed by oxygen is absorbed in the oxygen-containing layer.

7. The ultraviolet sterilizer according to claim 6, wherein a base end and the leading end of the cylindrical body are closed by the band pass filter and the irradiation window, and
the oxygen-containing layer is airtightly formed between the band pass filter and the irradiation window.

8. The ultraviolet sterilizer according to claim 6, wherein the band pass filter is provided at a position between the light guiding part and the lamp storage chamber, and the irradiation window is provided at a position of the light outputting leading end of the light guiding part.

9. The ultraviolet sterilizer according to claim 1, wherein the lamp storage chamber has a cylindrical body, and
at least one of an air exhaust fan and an air supply fan is provided at least one of one end and the other end of the cylindrical body in a cylinder axis direction thereof.

10. The ultraviolet sterilizer according to claim 9, wherein an ozone filter is provided in an air flow passage including at least one of the air exhaust fan and the air supply fan provided in the cylindrical body.

11. The ultraviolet sterilizer according to claim 1, wherein the ultraviolet light source is disposed to extend in an axial direction of the lamp storage chamber.

* * * * *